United States Patent
Llewellyn

(10) Patent No.: US 6,242,436 B1
(45) Date of Patent: Jun. 5, 2001

(54) USE OF 5ALPHA-ANDROSTANEDIOL OR 5ALPHA-ANDROSTANEDIONE TO INCREASE DIHYDROTESTOSTERONE LEVELS IN HUMANS

(76) Inventor: William Charles Llewellyn, P.O. Box 1162, Sound Beach, NY (US) 11789

( * ) Notice: Subject to any disclaimer, the term of this patent is extended or adjusted under 35 U.S.C. 154(b) by 0 days.

(21) Appl. No.: 09/594,569

(22) Filed: Jun. 15, 2000

(51) Int. Cl.[7] .................. A61K 31/568; A61K 3/5685
(52) U.S. Cl. .............................. 514/177; 514/178
(58) Field of Search ...................... 514/177, 178

(56) References Cited

U.S. PATENT DOCUMENTS 5,578,588 * 11/1996 Mattern et al. ............... 514/177
5,880,117 * 3/1999 Arnold ........................ 514/178

OTHER PUBLICATIONS

Goodman & Gilman's Pharmacological Basis of Therapeutics, 9th edition (McGraw–Hill), p. 1442, 1996.*

* cited by examiner

Primary Examiner—Phyllis G. Spivack

(57) ABSTRACT

This invention discloses a method of administering direct precursors of the hormone dihydrotestosterone as a means of increasing androgen levels in humans. As men age, a decline in androgenic hormone levels is typically noted, possibly resulting in muscle mass, bone density and energy loss. Various methods have therefore been developed to supplement androgens for men with declining levels. This invention teaches using precursors to testosterone, in that DHT and its precursors cannot be converted to estrogens in the human body. This may be a very advantageous trait for aging men at risk for benign prostatic hypertrophy, as estrogenic and androgenic action are both needed to induce this condition. As testosterone is the primary substrate for the synthesis of estradiol in men, its use as a target for androgen replacement may pose a greater health risk.

6 Claims, No Drawings

USE OF 5ALPHA-ANDROSTANEDIOL OR 5ALPHA-ANDROSTANEDIONE TO INCREASE DIHYDROTESTOSTERONE LEVELS IN HUMANS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

This invention relates a method of administering the dihydrotestosterone precursor hormone 5alpha-androstanediol or 5alpha-androstanedione as a means of increasing dihydrotestosterone levels in humans. Although testosterone is considered to be the primary male androgen, in many sites of action it is actually dihydrotestosterone that is the active form of this steroid. Dihydrotestosterone (DHT) is a more potent form of testosterone, shown to be roughly three to four times more active in the human body in comparison. Its higher level of activity is attributed to the ability of this hormone to bind to the androgen receptor with greater affinity, and with more stability, than testosterone. The activity of DHT is most closely related to the development and maintenance of male sexual characteristics, including external virilization, sexual maturity at puberty, spermatogenesis, sexual behavior/libido and erectile functioning. DHT has also been shown to be equally effective as testosterone at inducing the expected benefits of androgen replacement on mood, sexual function, bone and muscle.

A number of methods have been developed to restore androgen concentration in humans with declining levels. Several injectable esterified testosterone preparations have been fashioned that allow a slow release of hormone into the blood stream over the course of several days to weeks for example, however all provide inconsistent dosing as there is great variance in hormone release from the site of injection, such that a short supraphysiological rush may eventually be followed by days of subnormal hormone concentrations. The buildup of estrogens due to the natural process of aromatization may exaggerate the side effects to such medication, particularly at times when testosterone levels are abnormally high, as supraphysiological levels of estrogens in the male body have been linked to gynecomastia (female breast tissue development), water retention and edema, and increased fat deposition. More basically, recent studies have made clear that both androgens and estrogens play a synergistic role in the promotion of benign prostatic hypertrophy (BPH). This suggests that an aromatizable androgen such as testosterone may be less than ideal for use in older men at risk for such disease.

Also a number of synthetic oral androgen derivatives have been developed including methyltestosterone, fluoxymesterone and stanozolol. All such compounds are alkylated at the $17^{th}$ carbon position (alpha orientation), an alteration that inhibits reduction of the steroid to inactive 17-ketosteroid form. While this greatly improves oral bioavailability of the compound, this alteration has also been shown to place stress on the liver, in some instances resulting in organ damage. Although the use of a c-17 alpha alkylated oral androgen may prove much more comfortable for the patient in terms of dosing and control over blood hormone level compared to an injectable preparation, the possible risk of developing complications with liver functions may make them much less useful for androgen replacement compared to injectable preparations, particularly for extended periods of therapy.

In searching for a less toxic, more reliable oral alternative for androgen replacement the use of androgen precursor hormones have been suggested. U.S. Pat. No. 5,578,588 to Mattern et al. relates a method of using a precursor hormone, namely androstenedione, as a means of increasing testosterone levels. The pharmacokinetics of administering such a precursor are such that hormone concentrations of active hormone (testosterone) peak within 90 minutes, and subsequently decline over a period of three to four hours. This more closely resembles the natural pulsating pattern in which the body releases testosterone, and avoids the prolonged peaks and troughs noted with use of esterified injectable hormone preparations. Although the precursor hormone androstenedione discussed in this patent has been shown to effectively convert to testosterone after administration, it is also open to alteration by the aromatase enzyme. Its use may therefore result in an undesirable buildup of serum estrogen levels. This has been made clear in a recent study by Douglas King et al. (JAMA June; 1999 281(22):2020–28), which demonstrated that the rise in estrone and estradiol levels after administration of androstenedione was much more pronounced, and possibly more important physiologically, than that of testosterone.

U.S. Pat. No. 5,880,117 to Patrick Arnold. relates a method of using the precursor hormone 4-androstenediol as a means of increasing testosterone levels in humans. This hormone represents an improvement over androstenedione, as 4-androstenediol does not seem to be open to aromatase in its initial state. The possibility that this compound will preferentially convert to an estrogen over an androgen is likewise nonexistent. This compound also seems to convert to testosterone with greater efficacy than androstenedione, representing a second improvement of note in this invention. The end product testosterone however is still readily aromatized. So while the compound suggested in this patent does offer advantage over a previous patent in that the compound in question avoids a direct path of estrogen conversion and is more actively transformed to active state, the target hormone of replacement may still be less than ideal in many circumstances.

BRIEF SUMMARY OF THE INVENTION

U.S. Pat. Nos. 5,880,117 and 5,578,588 both relate novel methods of using direct precursor hormones to testosterone as a means of replacing androgen levels in men. Although the suggested practice of using a precursor to an active hormone seems quite sound, the target hormone of replacement in both patents (testosterone), however, may be less than idea in many cases due to its high rate of conversion to estrogen. The problem of the present invention is therefore to provide other naturally occurring androgenic hormone precursors that can be used to replace androgen action in humans but are devoid of undesirable estrogenic activity. According to the invention this problem is solved by the use of at least one precursor of dihydrotestosterone and which is preferably 5alpha-androstanediol or 5alpha-androstanedione. The mentioned precursors of dihydrotestosterone are ideal because they are natural, non-toxic, quickly metabolized to active form after oral administration and unable to be aromatized into estrogens due to their structure.

DETAILED DESCRIPTION OF THE INVENTION

The chemical term 5alpha-androstanediol refers to two isomers: 5alpha-androstane 3beta, 17beta diol and 5alpha-androstane 3alpha, 17beta diol. This invention concerns both isomer forms of 5alpha-androstanediol. 5alpha-androstanediol and 5alpha androstanedione are naturally occurring compounds. They have been identified as direct metabolites of dihydrotestosterone in placental, uterine, testicular, adrenal and nervous system tissues. They act as efficient precursors to dihydrotestosterone, converting to DHT via the 3-hydroxysteroid dehydrogenase (3alpha and 3beta HSD depending on isomer) and 17beta-hydroxysteroid dehydrogenase enzymes respectively.

Human tests carried out by Horst H J, Dennis M, Kaufmann J and Voigt K D (Acta Endocrinol (Copenh) June; 1975 79(2):394–402) have fundamentally proved the rapid transformation of tritiated 5alpha-androstanediol into dihydrotestosterone in vivo. In this study it was demonstrated that 30 minutes after intravenous injection of the 3alpha isomer, recovery of dihydrotestosterone was measured to be 54%, 23% and 43% in prostate, muscle and plasma respectively. After injection of the 3beta isomer, the recovery was measured to be 29%, 8% and 9% in prostate, muscle and plasma. With both compounds the principle metabolite produced was dihydrotestosterone. Studies by Stanczyk F, et al. (J. Steroid Biochem. Molec. Biol., 1990, 37(1):129–132) have fundamentally proved that 5-alpha androstanedione is also an important and direct precursor to dihydrotestosterone in the human body, converting to active form through a similar, yet distinct, metabolic pathway.

The idea of focusing on dihydrotestosterone as an androgen for replacement with men noticing declining androgen levels is also well supported in medical literature. A review by Bruno De Lignieres (Annals of Medicine (1993) 25:235–241), for example, covers successful studies in which transdermal DHT has been utilized with great success. The men undergoing such trails reaped the expected benefits of androgen replacement on mood, sexual functioning, without significant clinical or metabolic side effects. The risk for developing benign prostatic hypertrophy (BPH) may also be reduced with DHT (a non-aromatizable steroid) therapy compared to testosterone (the primary substrate for the synthesis of estradiol in men), as both androgenic and estrogenic stimulation is needed to induce this condition.

After discovering the efficiency in which both isomers of 5-alpha androstanediol, as well as 5-alpha androstanedione, convert to dihydrotestosterone in the human body, plus the suitability of dihydrotestosterone as a target for androgen replacement, it became the focus of this invention that one of the mentioned DHT precursors can be administered perorally as an effective means of raising dihydrotestosterone levels in humans. The oral daily dosage used should be 25 mg to 500 mg. Due to the rapidity in which the discussed compounds are metabolized in the body, the total daily dosage can be further subdivided for a more sustained blood hormone concentration, with 3–5 applications per day being most preferred. In addition to peroral use, 5-alpha androstanediol and 5-alpha androstanedione can be effectively administered by several other routes including transdermal, sublingual or intranasal. In order to increase bioavailability during sublingual or intranasal administration, the target hormone can additionally be complexed with a cyclodextrin, such as beta-hydroxypropyl-beta-cyclodextrin.

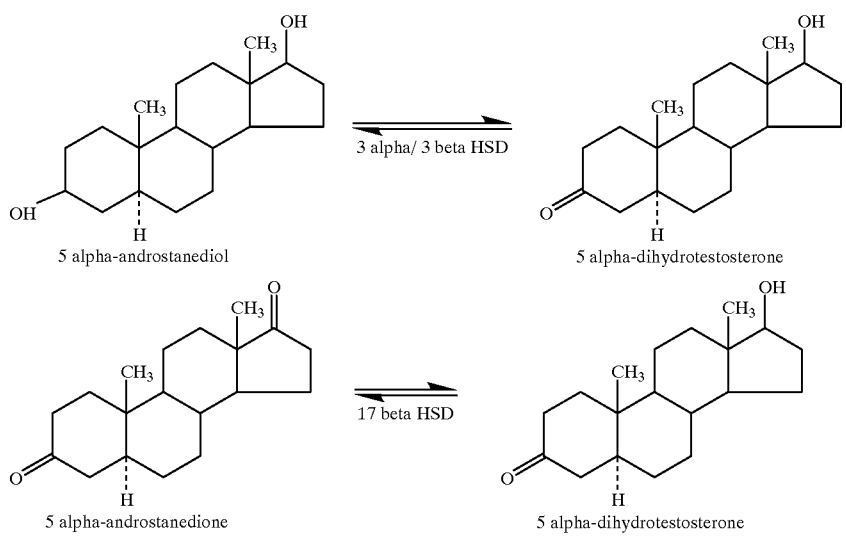

I claim:

1. The method of increasing dihydrotestosterone levels in humans by administration of 5-alpha androstanediol.

2. The method of increasing dihydrotestosterone levels in humans according to claim 1, wherein the 5-alpha androstanediol is 5-alpha androstane-3alpha, 17beta diol.

3. The method of increasing dihydrotestosterone levels in humans according to claim 1, wherein the 5-alpha androstanediol is 5-alpha androstane-3beta, 17beta diol.

4. The method of increasing dihydrotestosterone levels in humans by administration of 5-alpha androstanedione.

5. The method of increasing dihydrotestosterone levels in humans according to claim 1 or 2, wherein the mode of administration is peroral.

6. The method of increasing dihydrotestosterone levels in humans according to claim 1 or 2, wherein a peroral daily dosage of 25 mg to 500 mg is taken.

* * * * *